United States Patent
Zilberman et al.

(10) Patent No.: US 10,185,083 B2
(45) Date of Patent: Jan. 22, 2019

(54) COATED OPTICAL FIBRES HAVING IMPROVED FEATURES

(71) Applicant: ZDF LTD., Tiberias (IL)

(72) Inventors: Alexander Zilberman, Haifa (IL); Angelika Sokolowa, Tiberias (IL); David Mizrahi, Tiberias (IL)

(*) Notice: Subject to any disclaimer, the term of this patent is extended or adjusted under 35 U.S.C. 154(b) by 0 days.

(21) Appl. No.: 15/726,725

(22) Filed: Oct. 6, 2017

(65) Prior Publication Data
US 2018/0045884 A1    Feb. 15, 2018

Related U.S. Application Data

(62) Division of application No. 14/411,153, filed as application No. PCT/IL2013/050547 on Jun. 26, 2013.

(Continued)

(30) Foreign Application Priority Data

Jun. 26, 2012    (IL) .............................. 220657

(51) Int. Cl.
    *G02B 6/036*    (2006.01)
    *G02B 6/02*    (2006.01)
    (Continued)

(52) U.S. Cl.
    CPC .............. *G02B 6/036* (2013.01); *B01J 27/10* (2013.01); *B01J 27/13* (2013.01); *B01J 27/135* (2013.01);
    (Continued)

(58) Field of Classification Search
None
See application file for complete search history.

(56) References Cited

U.S. PATENT DOCUMENTS

| | | | |
|---|---|---|---|
| 5,079,600 A | | 1/1992 | Schnur et al. |
| 5,182,790 A | * | 1/1993 | Kayashima ........... C03B 37/023 385/141 |

(Continued)

FOREIGN PATENT DOCUMENTS

| | | |
|---|---|---|
| WO | WO 20020228551 A1 | 4/2002 |
| WO | WO 2013083600 A2 | 6/2013 |

OTHER PUBLICATIONS

Sun et al., "Uniform Silver Nanowires Synthesis by Reducing AgNO3 with Ethylene Glycol in the Presence of Seeds and Poly(Vinyl Pyrrolidone)", Chemistry of Materials, 2002, pp. 4736-4745, vol. 14, Issue 11, American Chemical Society, United States, Published Online Oct. 8, 2002.

(Continued)

*Primary Examiner* — Chad H Smith
(74) *Attorney, Agent, or Firm* — Knobbe, Martens, Olson & Bear, LLP

(57) ABSTRACT

A waveguide for high efficiency transmission of high energy light useful in ablation procedures at predetermined bandwidths over predetermined distances comprising: an optical fiber core; a silanization agent; layered cladding surrounding the optical fiber core comprising: a first thin metal layer comprising at least two types of metals the first thin metal layer covalently bonded to the core and a second thin metal layer bonded to the second metal layer, and a catalyst component; wherein the silanization agent comprising organofunctional alkoxysilane molecule, such as 3-aminopropyltriethoxysilane (APTS), is a self supporting bridge between the surface of the optical fiber and the first metal layer; the first metal layer is uniformly chemisorbed onto the surface of the optical fiber by means of covalent Si—O—Si bonds with the optical fiber; further wherein the catalyst compo- (Continued)

Figure 1:
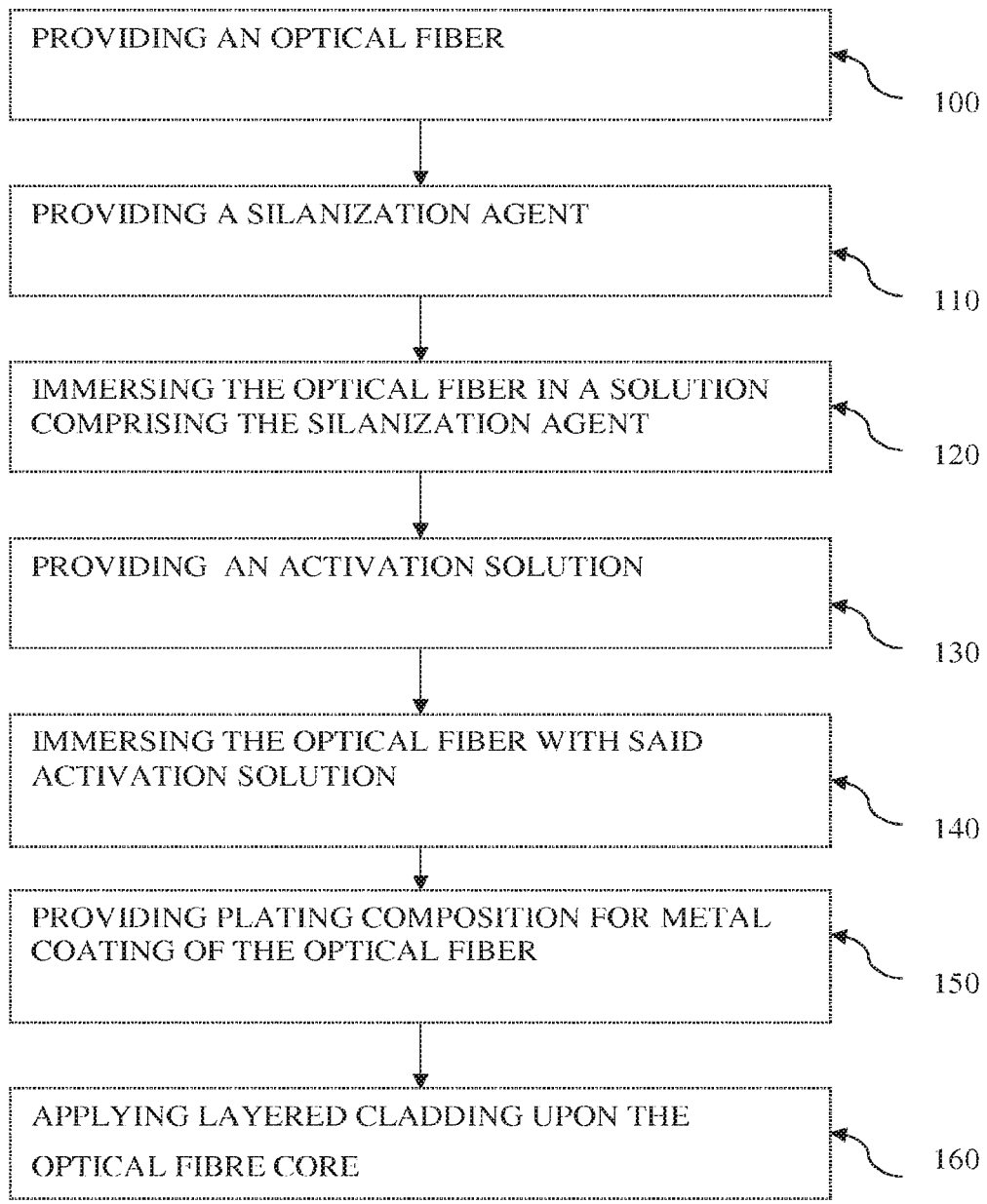

nent derived from an activation solution for enhancing the layered cladding upon the optical fiber.

7 Claims, 6 Drawing Sheets

Related U.S. Application Data

(60) Provisional application No. 62/083,232, filed on Nov. 23, 2014.

(51) Int. Cl.
| | |
|---|---|
| *G02B 6/44* | (2006.01) |
| *C23C 18/16* | (2006.01) |
| *B01J 27/13* | (2006.01) |
| *B01J 27/135* | (2006.01) |
| *B01J 27/10* | (2006.01) |
| *B01J 31/02* | (2006.01) |
| *C23C 28/02* | (2006.01) |
| *C23C 18/18* | (2006.01) |
| *C23C 18/32* | (2006.01) |
| *C23C 18/48* | (2006.01) |
| *C03C 25/1065* | (2018.01) |
| *C23C 18/28* | (2006.01) |
| *C23C 18/30* | (2006.01) |
| *C23C 18/36* | (2006.01) |
| *A61B 18/00* | (2006.01) |
| *A61B 18/22* | (2006.01) |

(52) U.S. Cl.
CPC ......... *B01J 31/0274* (2013.01); *C03C 25/109* (2013.01); *C23C 18/165* (2013.01); *C23C 18/1639* (2013.01); *C23C 18/1651* (2013.01); *C23C 18/1844* (2013.01); *C23C 18/1893* (2013.01); *C23C 18/285* (2013.01); *C23C 18/30* (2013.01); *C23C 18/32* (2013.01); *C23C 18/36* (2013.01); *C23C 18/48* (2013.01); *C23C 28/02* (2013.01); *G02B 6/02* (2013.01); *G02B 6/02033* (2013.01); *G02B 6/02395* (2013.01); *G02B 6/4478* (2013.01); *A61B 2018/00547* (2013.01); *A61B 2018/2222* (2013.01)

(56) References Cited

U.S. PATENT DOCUMENTS

| | | | |
|---|---|---|---|
| 5,500,315 | A | 3/1996 | Calvert et al. |
| 6,355,198 | B1 | 3/2002 | Kim et al. |
| 6,387,542 | B1 | 5/2002 | Kozlov |
| 6,451,009 | B1 | 9/2002 | Dasilva et al. |
| 6,709,755 | B2 * | 3/2004 | Ferm .................. C09D 4/00 427/387 |
| 2005/0141830 | A1 | 6/2005 | Peret |
| 2006/0079762 | A1 | 4/2006 | Norris et al. |
| 2013/0004778 | A1 * | 1/2013 | Tucker, III .......... C09D 183/14 428/426 |

OTHER PUBLICATIONS

Sun et al., "Large-Scale Synthesis of Uniform Silver Nanowires Through a Soft, Self-Seeding, Polyol Process", Advanced Materials, Jun. 5, 2002, pp. 833-837, vol. 14, Issue 11, Wiley-VCH Verlag GmbH, Weinheim.

Giersig et al., "Evidence of an aggregative mechanism during the formation of silver nanowires in N,N-dimethylformamide", Journal of Materials Chemistry, Feb. 2004, pp. 607-610, vol. 14 Issue 4, University of Vigo, Spain.

Jana et al., "Wet chemical synthesis of silver nanorods and nanowires of controllable aspect ratio", Chemical Communications, Jan. 2001, pp. 617-618, Department of Chemistry and Biochemistry, University of South Carolina, United States.

Hu et al., A simple and Effective Route for the Synthesis of Crystalline Silver Nanorods and Nanowires, Advanced Functional Materials, Feb. 2004, pp. 183-189, vol. 14, Issue 2, Wiley-VCH Verlag GmbH & Co, Weinheim.

Jia et al., Preparation of Microwave Absorbing Nickel-Based Activated Carbon by Electroless Plating with Palladium-Free Activation, BioResources; 2010, pp. 2248-2257, vol. 5 Issue 4.

Israeli Patent Office, International Search Report and Written Opinion dated Nov. 24, 2013 in corresponding International Application No. PCT/IL2013/050547, dated Nov. 24, 2013.

* cited by examiner

COATED OPTICAL FIBRES HAVING IMPROVED FEATURES

FIELD OF INVENTION

The present invention relates to electroless plated wave guides useful for ablation. More particularly, this invention pertains to a wave guide and production thereof.

BACKGROUND

Metal plating is a well-known process employed to alter the existing surface properties or dimensions of a substrate. A substrate may be plated for decorative purposes, to improve resistance to corrosion or abrasion, or to impart desirable electrical or magnetic properties to a substrate.

There are various methods of plating, including electroplating and electroless plating. Electroless plating involves the deposition of a metallic coating from an aqueous bath onto a substrate by a controlled chemical reduction reaction which is catalysed by the metal or alloy being deposited or reduced. This process differs from electroplating in that it requires no external electrical charge. One positive feature of electroless plating over electroplating is the ability to plate a substantially uniform metallic coating onto a substrate having an irregular shape. Frequently, electroplating an irregularly shaped substrate produces a coating having non-uniform deposit thicknesses because of varying distances between the cathode and anode of the electrolytic cell. Another positive feature of electroless plating over electroplating is that electroless plating is autocatalytic and continuous once the process is initiate, requiring only occasional replenishment of the aqueous bath. Also, electroless coatings are virtually nonporous, which allows for greater corrosion resistance than electroplated substrates.

In general, an electroless plating bath includes water, a water soluble compound containing the metal to be deposited onto a substrate, a complexion agent that prevents chemical reduction of the metal ions in solution while permitting selective chemical reduction on a surface of the substrate, and a chemical reducing agent for the metal ions. Additionally, the plating bath may include a buffer for controlling pH and various optional additives, such as bath stabilizers and surfactants.

Numerous methods have been used to grow metal nanowires. Among all the methods, solution-phase synthesis is one of the most promising routes to prepare ID nanostructure in terms of cost, throughput and the potential for high-volume production. In Y. G. Sun, Y. D. Yin, B. T. Mayers, T. Herricks, Y. N. Xia, *Chem. Mater.* 14, (2002), 4736., Y. G. Sun, Y. N. Xia. *Adv. Mater.* 14, (2002), 833 and M. Giersig, I. Pastoriza-Santos, L. M. Liz-Marz'an, *J. Mater. Chem.* 14, (2004), 607 poly (vinyl pyrrolidone) (PVP), silver nanowires were synthesized by organic solvent reduction such as ethylene glycol and N,N-dimethylfonnamide (DMF). Silver nanowires also had been synthesized in aqueous solutions. For instance, Murphy and co-workers in N. R. Jana, L. Gearheart, C. J. Murphy, *Chem. Commun.* 7, (2001), 617, had reported a process to synthesize silver nanorods by reducing AgNO3 with ascorbic acid. Zhang et al. also had reported a seed-less synthesis of silver nanowires using ascorbic acid as reducer in the presence of poly (methacrylic acid) (PMAA). In J. Q. Hu, Q. Chen, Z. X. Xie, G. B. Han, R. H. Wang, B. Ren, Y. Zhang, Z. L. Yang, Z. Q. Tan, *Adv. Funct. Mater.* 14, (2004), 183, Tan and co-workers had synthesized silver nanorods and nanowires by reduction of AgNO3 with tri-sodium citrate in the presence of dodecylsulfonate.

U.S. Pat. No. 6,387,542 also teaches a process for the electroless plating of silver onto a substrate using an aqueous plating bath comprising silver nitrate, ammonium hydroxide, ammonium carbonate and/or bicarbonate and hydrazine hydrate as a reducing reagent. The composition of the plating bath allows metallic silver to be precipitated from the plating bath by boiling in the form of sediment uncoated surface. There is therefore a long unmet need for improved metallized optical fibers.

SUMMARY

There is provided in accordance with a preferred embodiment of the present invention a waveguide for high efficiency transmission of high energy light useful in ablation procedures at predetermined bandwidths over predetermined distances comprising: (a) an optical fibre core, (b) a silanization agent; and (c) layered cladding surrouthending the optical fibre core comprising: (i) a first thin metal layer comprising at least two types of metals the first thin metal layer covalently bonded to the core; and, (ii) a second thin metal layer bonded to the second metal layer, (d) a catalyst component, wherein the silanization agent comprising organofunctional alkoxysilane molecule such as 3-aminopropyltriethoxysilane (APTS), is a self supporting bridge between the surface of the optical fibre and the first metal layer; the first metal layer is uniformly chemisorbed onto the surface of the optical fibre by means of covalent Si—O—Si bonds with the optical fibre; further wherein the catalyst component derived from an activation solution for enhancing the layered cladding upon the optical fiber.

There is further provided in accordance with a preferred embodiment of the present invention the wave guide as defined above, wherein the catalyst component is palladium, derived from an activation solution consisting of tin chloride, palladium chloride, potassium chloride.

There is further provided in accordance with a preferred embodiment of the present invention the wave guide as defined above, wherein the silanization agent consists of at least one amino group adapted as an adhesion enhancer component.

There is further provided in accordance with a preferred embodiment of the present invention the wave guide as defined above, wherein the activation solution combined with the APTS form metal-$NH_2$ and Pd—$NH_2$ covalent bonds such that the metal layer deposits rapidly upon the optical fibre.

There is further provided in accordance with a preferred embodiment of the present invention the wave guide as defined above, wherein the first metal layer is a thin metal coating of up to 3 microns in thickness and the second metal coating is up to 3 microns in thickness.

There is further provided in accordance with a preferred embodiment of the present invention the wave guide as defined above, wherein the first coating layer comprises silver and copper metals.

There is further provided in accordance with a preferred embodiment of the present invention the wave guide as defined above, wherein first metal applied on the surface of the tube is selected from the group consisting of: silver, nickel, aluminum, copper, gold, palladium, cobalt, and a combination thereof.

There is further provided in accordance with a preferred embodiment of the present invention the wave guide as defined above, wherein the optical fiber is coated with three different metals.

There is further provided in accordance with a preferred embodiment of the present invention the wave guide as defined above, wherein the optical fiber is coated with metal layers by means of electroless plating.

There is further provided in accordance with a preferred embodiment of the present invention the wave guide as defined above, wherein the optical fiber is selected from the group consisting of a plastic flexible tube, quartz flexible tube or a stainless steel tube.

There is further provided in accordance with a preferred embodiment of the present invention the wave guide as defined above, wherein the optical fiber material is selected from a group consisting of quartz, doped silica, glass or ceramic.

There is further provided in accordance with a preferred embodiment of the present invention the wave guide as defined above, wherein the first metal is silver.

There is further provided in accordance with a preferred embodiment of the present invention the wave guide as defined above, wherein second metal applied on the surface of the tube is selected from the group consisting of: silver, nickel, aluminum, copper, gold, palladium, cobalt, and a combination thereof.

There is further provided in accordance with a preferred embodiment of the present invention the wave guide as defined above, wherein the second metal is copper.

There is further provided in accordance with a preferred embodiment of the present invention the wave guide as defined above, wherein the activation solution is adapted as a metallization catalyst regent.

There is further provided in accordance with a preferred embodiment of the present invention the wave guide as defined above, wherein the second metal coating layer comprises nickel.

There is further provided in accordance with a preferred embodiment of the present invention the wave guide as defined above, wherein the activation solution is further provided as a catalysis metallization reaction of the second metal layer upon first metal layer.

There is further provided in accordance with a preferred embodiment of the present invention the wave guide as defined above, wherein the layered cladding is a uniform metal coating for applying over an optical fiber length of at least 50 cm.

There is further provided in accordance with a preferred embodiment of the present invention the wave guide as defined above, wherein the silanization agent provides a firm adhesion of the first metal layer upon the surface of the optical fiber There is further provided in accordance with a preferred embodiment of the present invention the wave guide as defined above, is adapted to be bent to an angle without substantial pinhole formation.

There is further provided in accordance with a preferred embodiment of the present invention the wave guide as defined above, is adapted to be bent to an angle without substantial energy losses.

There is further provided in accordance with a preferred embodiment of the present invention the wave guide as defined above, is adapted for prostate ablation, breaking stones procedure and other adjacent procedures.

There is further provided in accordance with a preferred embodiment of the present invention the wave guide as defined above, wherein the layered cladding prevents macro bending losses when the wave guide is coiled with a predetermined bend radius. The minimum bend radius will vary depending on the specific wave guide. However, in general, the minimum bend radius should not be less than ten times the outer diameter (OD) of the wave guide. If a tensile load is applied to the wave guide, as in the weight of the optical fiber in a long vertical run or an optical fiber that is pulled tightly between two points, the minimum bend radius is increased, due to the added stress.

The curvature radius of the bend is proximally within a range of 8 mm to 12 mm. There is further provided in accordance with a preferred embodiment of the present invention the wave guide as defined above, the waveguide is characterized by negligible macro-bending losses.

There is further provided in accordance with a preferred embodiment of the present invention the wave guide as defined above, further wherein the waveguide is with the ability to be bended to a predetermined angle without substantial pinhole formation.

There is further provided in accordance with a preferred embodiment of the present invention the wave guide as defined above, further wherein the wave guide has a non-circular and non-equilateral-polygonial outer cross-sectional shape adapted for bending in predetermined directions.

In accordance with a preferred embodiment of the present invention, the metal cladding layer is effective in protecting and preventing recessed tips (distal end) which are formed by erosion, during use, especially during straight firing. The metal coated layers are adapted as a protective covering which substantially extends the life of the wave guide when used in ablation procedures.

There is provided in accordance with a preferred embodiment of the present invention an electroless plating composition for coating an optical fiber comprising: (a) an aqueous solution for silver-copper activation surface comprising: (i) a silver salt, (ii) a copper salt, (iii) ammonium hydroxide, (iv) sodium and potassium tartrate, and (v) diethyldithiocarbamate, (iii) sodium hypophosphite, (iv) ammonium chloride. Wherein the electroless plating composition for coating an optical fiber further includes an activation solution consisting of tin chloride, palladium chloride and potassium chloride; further wherein higher adhesion coating of the silver-copper layer is formed by using a silanization agent comprising organofunctional an alkoxysilane molecule such as 3-aminopropyltriethoxysilane (APTS) as a self supporting bridge between the surface of the optical fibre and the first metal layer.

There is further provided in accordance with a preferred embodiment of the present invention the electroless plating composition as defined above, wherein the an aqueous solution for silver-copper activation surface comprises sodium and potassium tartrate or glucose. There is further provided in accordance with a preferred embodiment of the present invention the electroless plating composition as defined above, wherein the first metal layer is uniformly chemisorbed onto the surface of the optical fibre by means of covalent Si—O—Si bonds with the optical fibre; further wherein the silanization agent consists of amino group is adapted as an adhesion enhancer component There is further provided in accordance with a preferred embodiment of the present invention the electroless plating composition as defined above, wherein the activation solution consists of an electroless plating catalyst component.

There is further provided in accordance with a preferred embodiment of the present invention the electroless plating composition as defined above, wherein the copper salt is copper salt in the hydrate form.

There is further provided in accordance with a preferred embodiment of the present invention the electroless plating composition as defined above, wherein the copper is adapted for enhancing the adhesion of the silver salt upon the optical fiber.

There is provided in accordance with a preferred embodiment of the present invention an activation solution for catalyzing the coating reaction of the metal layers upon an optical fiber comprising: (a) tin chloride, (b)palladium chloride, and (c) potassium chloride, wherein the activation solution is adapted to provide a catalyst component combined with a silanization agent to further provide a self supporting bridge between the surface of an optical fibre and a metal layer; the silanization agent comprises an organofunctional alkoxysilane molecule such as 3-aminopropyltriethoxysilane (APTS).

There is further provided in accordance with a preferred embodiment of the present invention the activation solution as defined above, wherein the catalyst component is derived from the activation solution consisting of tin chloride, palladium chloride, potassium chloride.

There is further provided in accordance with a preferred embodiment of the present invention the activation solution as defined above, wherein the silanization agent consists of at least one amino group adapted as an adhesion enhancer component.

There is further provided in accordance with a preferred embodiment of the present invention the activation solution as defined above, wherein the APTS combined with the activation solution form covalent bonds of metal-$NH_2$ and Pd—$NH_2$ such that the metal layer deposits rapidly upon the optical fibre.

There is provided in accordance with a preferred embodiment of the present invention a method for plating metal layers upon a waveguide comprising the steps of: (a) providing an optical fiber, (b) providing a silanization agent, (c) immersing the optical fiber in a solution comprising the silanization agent, (d) providing an activation solution, (e) immersing the optical fiber in the activation solution; (f) providing plating composition for metal coating of the optical fiber comprising an aqueous solution, (g) applying layered cladding for surrounding the optical fibre core further comprising: (i) a first thin metal thin metal layer comprising at least two metals; the first thin metal is covalent bonded to the core; and, (ii) a second thin metal layer bonded to the second metal layer. Wherein the optical fiber is sensitized and catalytically activated by immersing the optical fiber in the activation solution; further wherein the silanization agent comprising an organofunctional alkoxysilane molecule such as 3-aminopropyltriethoxysilane (APTS), is a self supporting bridge between the surface of the optical fibre and the first metal layer; the first metal layer is uniformly chemisorbed onto the surface of the optical fibre by means of covalent Si—O—Si bonds with the optical fibre; further wherein the activation solution consists of palladium adapted as catalyst component for enhancing the layered cladding upon the optical fiber.

There is further provided in accordance with a preferred embodiment of the present invention the method as defined above, wherein the optical fiber is sensitized and catalytically activated by immersion into the activation solution.

There is further provided in accordance with a preferred embodiment of the present invention the method as defined above, wherein the metal layers adhesion enhancer component is derived from the APTS.

There is further provided in accordance with a preferred embodiment of the present invention the method as defined above, wherein the metal layers catalyst component is derived from the activation solution consisting of tin chloride, palladium chloride, potassium chloride There is further provided in accordance with a preferred embodiment of the present invention the method as defined above, the activation solution combined with the APTS form metal-$NH_2$ and Pd—$NH_2$ bonds such that the metal layer deposits rapidly upon the optical fibre.

There is further provided in accordance with a preferred embodiment of the present invention the method as defined above, wherein the activation solution is adapted as a metallization catalyst regent.

There is further provided in accordance with a preferred embodiment of the present invention the method as defined above, wherein the first metal layer is a thin metal coating of up to 3 microns in thickness and the second metal coating is up to 3 microns in thickness.

There is further provided in accordance with a preferred embodiment of the present invention the method as defined above, wherein the first coating layer comprises silver and copper metals.

There is further provided in accordance with a preferred embodiment of the present invention the method as defined above, wherein the first metal is silver metal.

There is further provided in accordance with a preferred embodiment of the present invention the method as defined above, wherein the optical fiber is coated with three different metal layer.

There is further provided in accordance with a preferred embodiment of the present invention the method as defined above, wherein the optical fiber is a flexible tube.

There is further provided in accordance with a preferred embodiment of the present invention the method as defined above, wherein the optical fiber is selected from the group consisting of a plastic flexible tube, quartz flexible tube or a stainless steel tube.

There is further provided in accordance with a preferred embodiment of the present invention the method as defined above, wherein the optical fiber material is selected from the group consisting of quartz, doped silica, glass or ceramic.

There is further provided in accordance with a preferred embodiment of the present invention the method as defined above, wherein the second metal layer is nickel.

There is further provided in accordance with a preferred embodiment of the present invention the method as defined above, wherein the activation solution is further provided for catalysis reaction of metallization of the second metal layer.

There is further provided in accordance with a preferred embodiment of the present invention the method as defined above, wherein the uniform coating is applied over the optical fiber length of at least 50 cm.

There is further provided in accordance with a preferred embodiment of the present invention the method as defined above, wherein the silanization agent provides a firm adhesion on the surface of between the optical fiber surface, the first metal and the second metal.

There is further provided in accordance with a preferred embodiment of the present invention the method as defined above, wherein the activation solution provides a catalystic effect of plating the first metal layer upon the surface and the second metal layer.

There is further provided in accordance with a preferred embodiment of the present invention the method as defined above, further wherein the waveguide is with the ability to be bended to a predetermined angle without substantial pinhole formation.

There is further provided in accordance with a preferred embodiment of the present invention the method as defined above, further wherein the waveguide is adapted to be bent to a a predetermined angle without substantial energy losses.

There is further provided in accordance with a preferred embodiment of the present invention the method as defined above, further wherein the waveguide is adapted for prostate ablation or other adjacent procedures.

BRIEF DESCRIPTION

Figure 2:
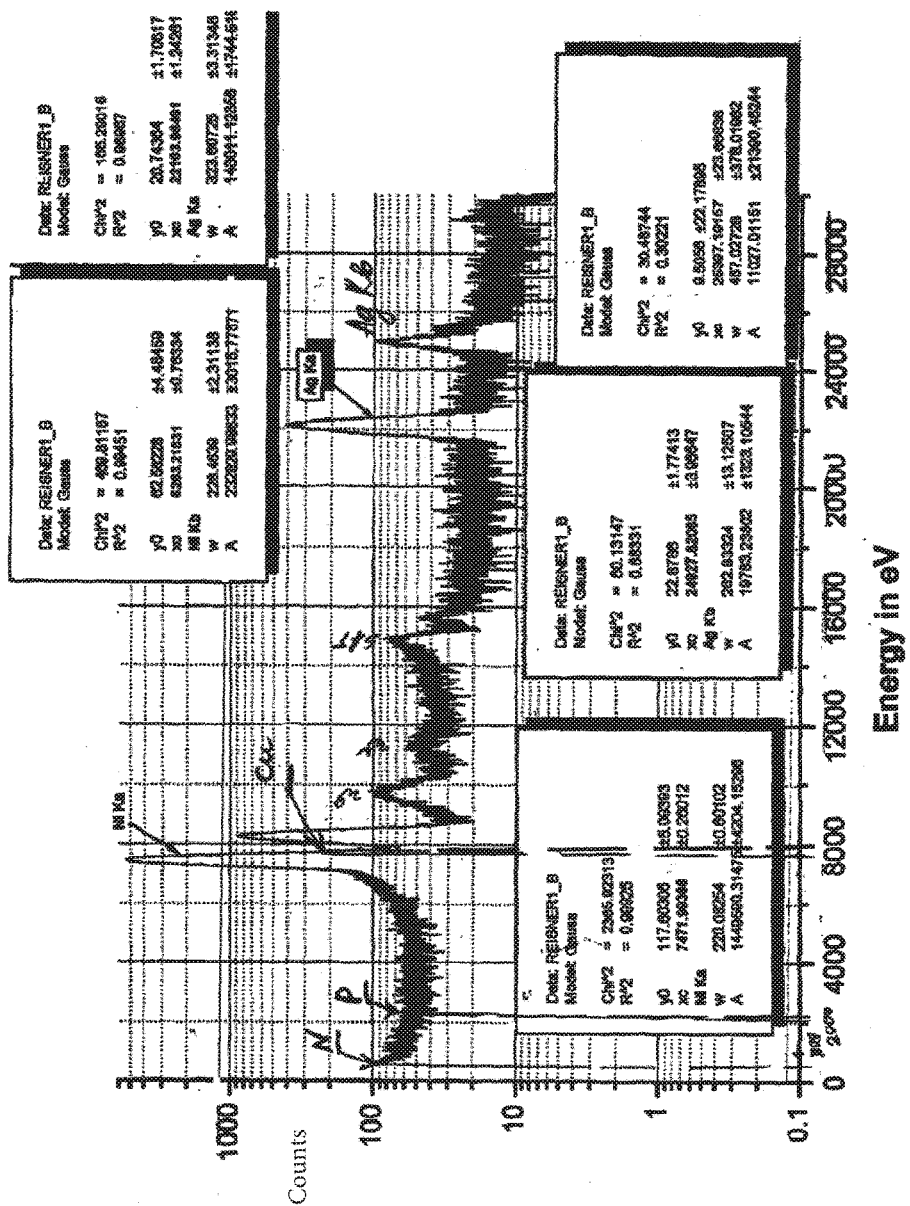
Figure 3:
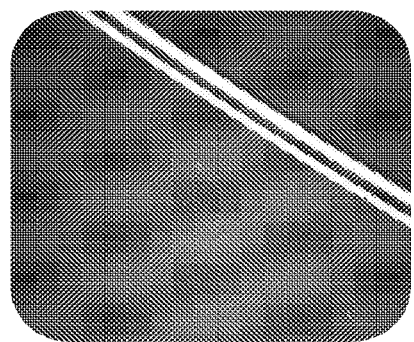
Figure 4:
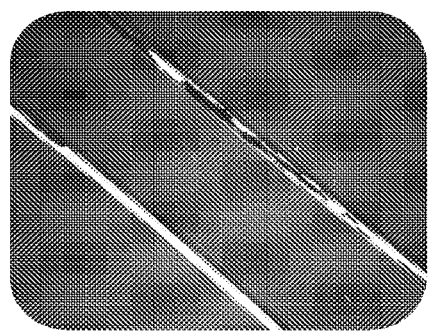
Figure 5:
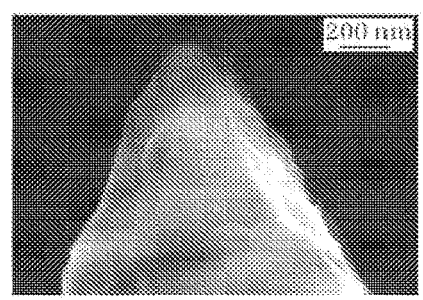
Figure 6:
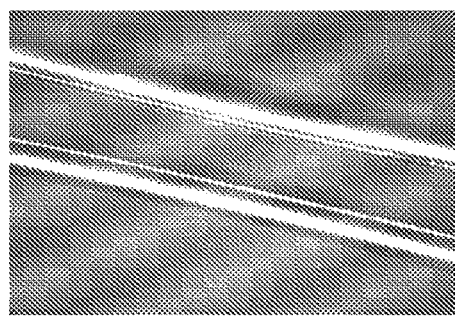

In order to understand the invention and to see how it may be implemented in practice, a few preferred embodiments will now be described, by way of non-limiting example only, with reference to be accompanying drawings, in which:

FIG. 1 presents a flow chart of the method for plating an optical fiber, in accordance with a preferred embodiment of the present invention;

FIG. 2 presents a XRF graph of the waveguide, in accordance with a preferred embodiment of the present invention;

FIG. 3 presents an optical microscope image of the optical fiber after metal electroless plating, in accordance with a preferred embodiment of the present invention;

FIG. 4 presents an optical microscope image of the optical fiber after metal electroless plating, in accordance with a preferred embodiment of the present invention;

FIG. 5 presents a scanning electron microscopy image of the optical fiber after metal electroless plating, in accordance with a preferred embodiment of the present invention; and FIG. 6 presents an optical microscope image of the optical fiber after metal electroless plating, in accordance with a preferred embodiment of the present invention.

DETAILED DESCRIPTION

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a wave guide for transmission of light energy. The wave guide is coated with metal layers by an aqueous synthesis process. The present invention provides a waveguide and methods of production thereof resulting in waveguides which are smooth and free of pinholes, with a uniform metal coating.

It is herein acknowledged that the term optical fibre and probe are equivalent in meaning in the present description.

The present invention provides a waveguide useful for transmitting high amounts of energy over distance with a minimum of losses. Another object of the invention is to provide a method for making such a waveguide.

The waveguide of the present invention is a dielectric waveguide (that transmits light along its axis, by the process of total internal reflection. The waveguide consists of a core surrounded by a cladding layer. In order to confine the optical signal in the core, the refractive index of the core is greater than that of the cladding. The boundary between the core and cladding may either be abrupt, in step-index fiber, or gradual, in graded-index fiber. The optical fiber core is prepared by etching of chromic acid base of hydrofluoric acid base solutions and/or ethoxysilanes based primers selected from the group consisting of Triethoxy(ethyl)silane, dimethylaminosilane, Chloromethylethoxydimethylsilane, γ-Aminopropyltriethoxysilane and a combination thereof.

The present invention is directed to a wave guide for high efficiency transmission of light over distances greater than 3 meters at predetermined bandwidths comprising:

(a) an optical fibre core, (b) a silanization agent; and (c) layered cladding surrounding the optical fibre core further comprising: (i) a first thin metal layer comprising at least two types of metals. The first metal layer is covalent bonded to the core, and (ii) a second thin metal layer bonded to the first metal layer, (d) a catalyst component. The silanization agent is a self supporting bridge between the surface of the optical fibre and the first metal layer comprising an organofunctional alkoxysilane molecule such as 3-aminopropyltriethoxysilane (APTS). The first metal layer is uniformly chemisorbed onto the surface of the optical fibre by means of covalent Si—O—Si bonds with the optical fibre. The catalyst component is palladium derived from an activation solution for enhancing the layered cladding upon the optical fiber. Another embodiment of the present invention, the distance between the proximal end and the distal end of the optical fiber is about 50 cms.

The present invention presents the effect of the primer 3-aminopropyltriethoxysilane (APTS) and combined activator $SnCl_2$, $PdCl_2$, KCl on the plating efficiency of the metallization reaction and of the activation of the optical fibre surface. Another embodiment of the present invention, the catalyst component is derived from an activation solution consisting of tin chloride, palladium chloride, potassium chloride. The activation solution combined with APTS form metal-$NH_2$ and Pd—$NH_2$ covalent bonds such that the metal layers deposits rapidly upon the optical fibre.

Further more the silanization agent is preferably comprising APTS but could be of other solutions for making of Si—O—Si self supporting bridge, this solutions includes:

1-trimethylsilyl(methyl)benzotriazole 4% wt, in C2H5OH:H2O (50:50). This solution like in chemical activity to solution of APTS and can use both solutions, and one of them in our process, but APTS best.

Another embodiment of the present invention, the optical fiber is a tube which may be of flexible polyethylene having an internal diameter of about 450 µm, an external diameter of at least 6 mm. Other types of plastic materials could be used, including polypropylene, polystyrene, fluoropolymers, polyamides (e.g., nylon 6, nylon 11), polyurethanes, natural or synthetic rubber, silicone rubber and polyvinyl chloride. The dimensions of the optical fiber can be varied; also its cross-section can have different geometrical shapes, besides the circular shape illustrated, including square, rectangular or ellipsoidal.

The optical fiber communicator may also be of rigid material, such as quartz, doped silica, or of metal, such as stainless steel. When metal is used, particularly stainless steel, it is preferred to apply a coating of copper, by electroless technique, as the primary layer onto the surface of the tube.

Another embodiment of the present invention, the fiber electroless plating comprises three different metals. The first metal coating applied on the surface of the tube is preferably of silver (in a Glucose or sodium potassium tartrate system), but could be of other metals, including nickel (in a hypophosphite system), aluminum, copper (in a formaldehyde system), gold (in a borohydride system), palladium, cobalt (in a hypophosphite system), and a combination thereof.

The first coating layer further comprises a small amount of copper as additional metal while the combination of silver-copper coating layer is with a thickness preferably up to 3 microns. The additional metal of copper is further adapted for enhancing the adhesion of silver layer upon the optical fibre and further enhancing the adhesion of the second coating layer upon the first layer. The first coating layer is formed upon the optical fibre by bringing the optical fiber into contact with a silver-copper plating solution. Further more the additional metal is preferably copper but could be of other metals such as Sb for increasing the adhesion effect of Ag to the optical fiber surface.

The optical fiber is provided with a unique coating, free of pinholes. The coating comprises a silver-copper layer of only 3 microns thickness, and a second layer comprising nickel of about 3 to 20 microns thickness, such that a bright mirror of Ag—Cu, Ni coating of about 8 to about 9 micron of thickness is obtained. The preferred thickness is between 0.25 to about 5 microns.

The second metal coating layer applied on the surface of the tube is preferably of nickel, but could be of other metals, including silver, aluminum, copper, gold, palladium, cobalt, and a combination thereof.

The layered cladding is a uniform metal coating over a length of at least 50 cm, and has almost perfect reflection (mirror effect), such that a very little or no energy escapes from the fiber, energy losses are very low, and the efficiency of energy transfer from the laser generator to the target is high. Operationally, the coating prevents escape of light energy by not forming "pinholes" through the cladding, even during bending of the fibre.

The unique plating of the present invention is achieved by an electroless plating process, specifically, the optical fiber is consecutively coated with silver, copper and nickel by means of electroless plating. The metallization process is a controlled synthesis of each of the coating layers, for providing the optimal combination for the fiber of overall diameter, flexibility, energy transfer to target and minimal energy loss.

The process provides a self-supporting bridge combined with an activation solution that improves the adhesion of the silver-copper coating layer is with a thickness preferably up ride. The self supporting bridge combined with activation solution are used for the metallization of the silver-copper layer. The activation solution is further adapted for metallization of nickel layer.

In the another embodiment of the present invention, the process optimizes the flexibility of the coated fibre without any loss of the integrity of the coating layer such that waveguide is bended to a bending angle and no light energy losses, which is needed for prostate ablation, breaking stones procedure and similar procedures.

In the preferred embodiment of the invention, the silver nitrate and copper sulphate penta-hydrate are water soluble. The preferred complexion agents are ammonium hydroxide ($NH_4OH$) and Ethyldiamine. The preferred reducer is Sodium, potassium tartrate which reduce Silver nitrate ($AgNO_3$) in the presence of Copper sulphate pentahydrate ($CuSO_4 \times 5H_2O$). The preferred stabilizer is Diethyldithiocarbamate.

Catalytically inactive materials like glass, ceramics and polymers can be activated by conventional methods, for instance by contacting with a tin salt solution and/or a noble metal solution. The process is continuous and can be maintained for virtually an infinite time by merely replenishing each of the components of the bath.

Silver is a desirable reflective plating metal for its high electrical conductivity, corrosion resistance and good friction and wear properties.

Another embodiment of the present invention, a second solution is used for coating the second metal plating layer. The preferred second metal plating is nickel, for this reaction the preferred compound is a Nickel chloride. The preferred complexion agent is Sodium citrate dehydrate. The preferred reducer is Sodium hypophosphite which reduces Nickel chloride ($NiCl_2$). The preferred stabilizer is Ammonium chloride.

Plating of Ni layer may further performed by electrical transmission combined with electroplating solution.

Accordingly, the preferred plating bath mechanism can be described by the following general formula:

A) Electroless plating of Silver, Copper layer:

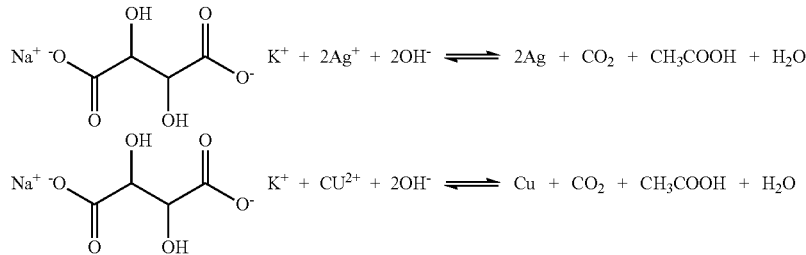

Silver-Copper layer on the surface of optical fiber, thus highly Silanization of the metal layer on the surface of the optical fiber. Silanization is formed with organofunctional alkoxysilane molecule of 3-amino propyl triethoxy silane B) Electroless plating of Ni layer:

The electroless silver plating onto probe surface using a self-supporting bridge is illustrated by the following:

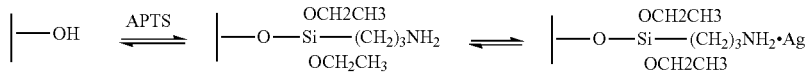

(APTS) combined with an activation solution which comprises tin chloride, palladium chloride and potassium chloride.

The mechanism for metallization of optical fibre probes is illustrated in the scheme above. APTS, an excellent silanization reagent, is quickly chemisorbed onto the hydroxylated probe surface of optical fibre, via strong covalent bonds of Si—O—Si and forms homogenous compact ultra thin layer on the surface, with free —$NH_2$ radicals outwards. The —$NH_2$ is attacked by Ag and forms an Ag$NH_2$ complex, which leads to Ag chemisorbed onto the probe surface firmly. Ag is quickly deposited onto the probe surface according to the scheme of traditional electroless plating by Ag—Ag interactions.

The electroless plating method of the present invention further provide a wavelength with a decreased optical bending radius, increase transmission energy and decreased treatment time.

The novel and unique electroless plating method for producing a Silver-Copper layer upon an optical fiber was compared with other plating methods, such as APTS-modified and unmodified optic fibers. Optical microscopy analysis after a plating time of 60 min showed that the concentration of Ag is larger on the APTS-modified optic fibres than on the unmodified ones. The plating of the APTS-modified probes originates from Ag attacked-$NH_2$ as previously mentioned, while the Ag coating of the unmodified probes depends on physical absorption at the beginning of electroless plating process. This absorption is determined by presence of activated palladium atoms, since Ag and Pd reacts quickly with —$NH_2$ to form Ag—$NH_2$ and Pd—$NH_2$ bonds, then the APTS-modified probes sensitize quickly, and Ag deposits rapidly according to the scheme of traditional electroless plating. In this way the silver mirror is formed. In contrast, the plating rate of the unmodified probes is restricted by physical absorption of Ag slowly onto the probes surface.

Another embodiment of the present invention, an electroless plating composition for coating an optical fiber is provided, comprising: (a) an aqueous solution for silver copper activation surface comprising; (i) a silver salt, (ii) a copper salt, (iii) ammonium hydroxide, (iv) sodium and potassium tartrate and (v) diethyldithiocarbamate
(b) an aqueous solution for nickel activation surface comprising:
(i) nickel chloride, (ii) sodium citrate dehydrate, (iii) sodium hypophosphite and (iv) ammonium chloride. The electroless plating composition for coating an optical fiber further includes an activation solution consisting of tin chloride, palladium chloride and potassium chloride; further wherein higher adhesion coating of the silver-copper layer is formed by using a silanization agent comprising organofunctional an alkoxysilane molecule such as 3-aminopropyltriethoxysilane (APTS) as a self supporting bridge between the surface of the optical fibre and the first metal layer Another embodiment of the invention the electroless plating composition as described above, wherein the first metal layer is uniformly chemisorbed onto the surface of the optical fibre by means of covalent Si—O—Si bonds with the optical fibre. Further wherein the silanization agent consists of at least one amino group is adapted as an adhesion enhancer component.

Another embodiment of the invention the electroless plating composition as described above, wherein the copper salt is copper salt in the hydrate form.

Another embodiment of the present invention, an activation solution for adhesion of metal layer upon an optical fiber is provided, comprising: (a) tin chloride, (b) palladium chloride, and (c) potassium chloride.

The activation solution is adapted to provide an activation enhancer combinable with a silanization agent to further provide a self supporting bridge between the surface of an optical fibre and a metal layer comprising organofunctional an alkoxysilane molecule such as 3-aminopropyltriethoxysilane (APTS).

Another embodiment of the invention the an activation solution as described above, wherein the APTS form metal-$NH_2$ and Pd—$NH_2$ covalent bonds such that the metal layer deposits rapidly upon the optical fibre. Further more the amino group derived from the APTS acts as an adhesion enhancer component of metal plating upon the optical fiber.

Reference is now made to FIG. 1 which illustrates a schematic diagram of a method for plating metal layers upon a waveguide comprising steps of:

(a) providing an optical fiber 100, (b) providing a silanization agent 110, (c) immersing the optical fiber in a solution comprising the silanization agent 120, (d) providing an activation solution 130, (e) immersing the optical fiber in the activation solution 140, (f) providing plating composition for metal coating of the optical fiber comprising an aqueous solution 150, (g) applying layered cladding for surrounding the optical fibre core 160 further comprising: (i) a first thin metal thin metal layer comprising at least two metals; the first thin metal is covalent bonded to the core; and (ii) a second thin metal layer bonded to the second metal layer. The silanization agent comprising organofunctional an alkoxysilane molecule such as 3-aminopropyltriethoxysilane (APTS), is a self supporting bridge between the surface of the optical fibre and the first metal layer. The first metal layer is uniformly chemisorbed onto the surface of the optical fibre by means of covalent Si—O—Si bonds with the optical fibre. Furthermore the activation solution comprises a catalyst component Another embodiment of the invention the method as described above, wherein the optical fiber is sensitized and catalytically activated by immersion into the activation solution.

Another embodiment of the invention the method as described above, wherein the metal layers adhesion enhancer component is derived from the silanization agent.

Another embodiment of the invention the method as described above, wherein the metal layers catalyst component is palladium derived from an activation solution consisting of tin chloride, palladium chloride, potassium chloride.

Another embodiment of the invention the method as described above, wherein the activation solution combined with the APTS form metal-$NH_2$ and Pd—$NH_2$ covalent bonds such that the metal layer deposits rapidly upon the optical fibre.

Another embodiment of the invention the method as described above, wherein the activation solution is adapted as a metallization catalyst regent.

Another embodiment of the invention the method as described above, wherein the first metal layer is a thin metal coating of up to 3 microns in thickness and the second metal coating is up to 3 microns in thickness.

Another embodiment of the invention the method as described above, wherein the first coating layer comprises silver and copper metals.

Another embodiment of the invention the method as described above, wherein the first metal is silver metal.

Another embodiment of the invention the method as described above, wherein the optical fiber is coated with three different metals.

Another embodiment of the invention the method as described above, wherein the optical fiber is a flexible tube.

Another embodiment of the invention the method as described above, wherein the optical fiber is selected from the group consisting of a plastic flexible tube, quartz flexible tube or a stainless steel tube.

Another embodiment of the invention the method as described above, wherein the optical fiber material is selected from the group consisting of quartz, doped silica, glass or ceramic.

Another embodiment of the invention the method as described above, wherein the second metal layer is nickel.

Another embodiment of the invention the method as described above, wherein the activation solution is further provided for catalysis reaction of metalization of the second metal layer.

Another embodiment of the invention the method as described above, wherein the uniform coating is applied over the optical fiber length of at least 50 cm.

Another embodiment of the invention the method as described above, wherein the activation solution provides a firm adhesion on the surface of between the optical fiber surface, the first metal and the second metal.

Another embodiment of the invention discloses and provides the method as described above, wherein the activation solution provides a catalytic effect of plating the first metal layer upon the surface and the second metal layer.

Another embodiment of the invention the method as described above further discloses and provides wherein the waveguide is with the ability to be bended to an angle without substantial energy losses.

Another embodiment of the invention provides and discloses the method as described above, further wherein the waveguide is adapted for prostate ablation or other adjacent procedures.

There is further provided in accordance with a preferred embodiment of the present invention the wave guide as defined above, wherein the layered cladding prevents macro bending losses when the wave guide is coiled with a bend radius. There is further provided in accordance with a preferred embodiment of the present invention the wave guide as defined above, the waveguide is characterized by negligible macro-bending losses.

There is further provided in accordance with a preferred embodiment of the present invention the wave guide as defined above, further wherein the waveguide is with the ability to be bended to an angle without substantial pinhole formation.

There is further provided in accordance with a preferred embodiment of the present invention the wave guide as defined above, further wherein the wave guide has a non-circular and non-equilateral-polygonial outer cross-sectional shape adapted for bending in predetermined directions.

EXAMPLE 1

The probe is cleaned by 3% w $K_2Cr_2O_7$, $H_2SO_4$ (conc) solution, treated by chemical etching with 20% w HF (70%), 40% w $H_2SO_4$ (conc) etching solution at 50 C.° for 6 min and subsequently rinsed thoroughly with deionized water. The hydroxylated probe was immersed immediately into 4% w 3-aminopropyltrietoxysilane (APTS), 50:50 $H_2O$: $C_2H_5OH$ solution for 20 min at 60 C.° to form amino-propyl self-supported monolayers. Then, the probe was rinsed thoroughly with deionized water.
  a) The probe is sensitized and catalytically activated by immersion for 6-10 min into solution of activation (40 g/l $SnCl_2$, 1 g/l $PdCl_2$, 140 g/l KCl, 75 ml/l HCl), rinsed with deionized water, 2% NaOH, deionized water.
  b) The probe is immersed for 30-60 min t=40-50 C.° in an electroless Ag, Cu plating bath containing 2 g/l Ag as $AgNO_3$, 12 ml/l $NH_4OH$, sodium, potassium tartrate 1.5 g/l, Ethylendiamine 0.1 g/l. Diethyldithiocarbamate 0.001 g/l, $CuSO_4 \times 5H_2O$ 0.1 g/l.

A bright mirror Ag,Cu coating of 3 micron thick was obtained. Samples are treated with baking process (temp.=100 C.°, Vacuum 70 cm, 1 hour).

The probe was sensitized and catalytically activated by procedure a) and then immersed for 30-60 min in an electrolles Ni plating bath containing 45 g/l $NiCl_2 \times 6H_2O$, 20 g/l $NaH_2PO_2 \times H_2O$, 45 g/l sodium citrate dihydrate, 50 g/l $NH_4Cl$ at 80 C.°, pH 5-5.5.

A bright mirror Ag, Ni coating of 5-6 micron thick was obtained.

Scanning electron microscope images were obtained on a LEO 1530 type microscopy (Leone, Germany).

Such a silver, nickel coating is useful for glass fiber optical wave-guides and as a conductive path in electronic components.

Reference is now made to FIG. 2 which illustrates a XRF (X Ray Fluorescence) analysis of the waveguide of the present invention with plating time of 60 min of Copper, Silver and 60 min plating time of Nickel on optical fiber.

The analysis shows the fluorescent spectral lines of the metal coating layers upon the optical fiber of the present invention. It can be seen that silver and nickel are the main elements of the metal coating layers. The identification of the other elements, which are in a lower concentration, was based on the reference: http://xdb.lbl.gov/Section1/Periodic Table/X-ray Elements.html; Jia and Wang (2010). "Nickel-based activated carbon". BioResources 5(4), 2248-2257

The electron binding energy range of the different elements was identified as follow:
N $K\alpha$=392.4 cV; P $K\alpha$=2,013.7 cV; $K_\beta$=2,139.1 cV; Cu $K\alpha$=8,047.78 eV; $K_\beta$=8,905.29 eV.

FIG. 3 presents an optical microscope image (×75) of the probe shows optical fiber with silver, copper coating on the surface after 30 min electrolles silver plating, with application of APTS self-supporting bridge and the activation solution.

FIG. 4. presents an optical microscope image (×75) of the probe shows optical fibre with silver, copper coating on the surface after 30 min electrolles silver plating, without application of APTS self-supporting bridge and the activation solution.

FIG. 5. presents a scanning electron microscopy image of a probe apex area after 60 min electroless silver, copper plating.

FIG. 6. presents an optical microscope image (×75) of the probe show optical fibre with Silver, Copper and Nickel coating on the surface after Silver, Copper plating, and after 60 min Nickel plating.

The invention claimed is:
1. A waveguide for high efficiency transmission of high energy light for ablation procedures at predetermined bandwidths over predetermined distances, comprising:
  a. an optical fibre core;
  b. an alkoxysilane bridge derived from 3-aminopropyltri-ethoxy-silane, immobilized onto the optical fibre core via covalent Si-O-Si bonds with said optical fibre core, and capable of binding metals with its amino functional group; and
  c. a metal-layered cladding bound to the alkoxysilane bridge, thereby coating said optical fibre core with metals, said metal-layered cladding consisting of:

i. a first thin metal layer including a plurality of metals, said first thin metal layer of up to 3 microns in thickness bound to said core; and ii. a second thin metal layer of up to 3 microns in thickness bound to said first metal layer;

wherein (i) said metal-layered cladding has a thickness between 0.25 to about 5 micron, and (ii) said waveguide has a bending radius in a range of 8 mm to 12mm without pinhole formation.

2. The waveguide according to claim 1, wherein said first thin metal layer comprises metals selected from silver, nickel, aluminum, copper, gold, palladium, cobalt or a combination thereof.

3. The waveguide according to claim 2, wherein said first thin metal layer comprises silver and copper metals.

4. The waveguide according to claim 1, wherein said optical fibre core is selected from the group consisting of a plastic flexible tube, quartz flexible tube or a stainless steel tube; or material of said optical fibre core is selected from the group consisting of quartz, doped silica, glass or ceramic.

5. The waveguide according to claim 1, wherein said second thin metal layer is selected from the group consisting of silver, nickel, aluminum, copper, gold, palladium, cobalt or a combination thereof.

6. The waveguide according to claim 5, wherein said second thin metal layer comprises nickel.

7. The waveguide according to claim 1, wherein the alkoxysilane bridge is positioned between the optical fibre core and the metal-layered cladding.

* * * * *